United States Patent
Berry, Jr.

[11] Patent Number: 6,010,670
[45] Date of Patent: Jan. 4, 2000

[54] STERILIZATION ASSEMBLY FOR INSTRUMENT CASE

[76] Inventor: Bernie B. Berry, Jr., 5315 E. Pleasant Run Parkway South Dr., Indianapolis, Ind. 46219

[21] Appl. No.: 09/089,692

[22] Filed: Jun. 3, 1998

[51] Int. Cl.$^7$ .................. A61L 2/20; A61L 2/00
[52] U.S. Cl. .................. 422/295; 422/113; 422/292; 206/439; 220/4.26
[58] Field of Search .................. 422/2, 25–28, 422/105, 112, 113, 292, 295, 297, 298, 300, 305, 296, 310; 206/439; 220/4.26

[56] References Cited

U.S. PATENT DOCUMENTS

| | | | |
|---|---|---|---|
| 3,734,342 | 5/1973 | Patterson | 220/4.26 |
| 4,251,482 | 2/1981 | Sanderson et al. | 422/296 |
| 4,372,921 | 2/1983 | Sanderson et al. | 422/296 |
| 4,416,417 | 11/1983 | Sanderson et al. | 422/310 |
| 4,748,003 | 5/1988 | Riley | 422/296 |
| 4,971,774 | 11/1990 | Schwanke et al. | 422/296 |
| 5,678,716 | 10/1997 | Umiker | 220/4.26 |

*Primary Examiner*—Robert J. Warden, Sr.
*Assistant Examiner*—Fariborz Moazzam
*Attorney, Agent, or Firm*—Woodard, Emhardt, Naughton, Moriarty & McNett

[57] ABSTRACT

A sterilization assembly for sterilizing an instrument case which is loaded with medical and/or dental instruments includes three primary components which are similarly arranged with flange surfaces and part-circular bosses which define bolt clearance holes. These three components include a base configured with receiving pockets for retaining a liquid sterilant, a collar and a lid which includes a pressure-relief valve. Positioned between the base and the collar is a first elastomeric gasket. Positioned between the lid and the collar is a second elastomeric gasket. By the use of bolts and threaded inserts, the lid and base are securely clamped together, sandwiching therebetween the collar and the two gaskets. This securely joined combination defines a hollow interior which receives therein at least one instrument case. By heating the liquid sterilant to a sufficiently high temperature, a sterilant vapor is created. As the vapor pressure builds, the instruments in the instrument case are sterilized. The pressure-relief valve which is in a normally closed condition is allowed to open once the interior pressure reaches a sufficiently high level which coincides with sterilization. Once a portion of the sterilant vapor is vented, the pressure decreases and the relief valve closes. This creates a tightly sealed assembly with a sterilized instrument case and sterilized instruments inside.

25 Claims, 8 Drawing Sheets

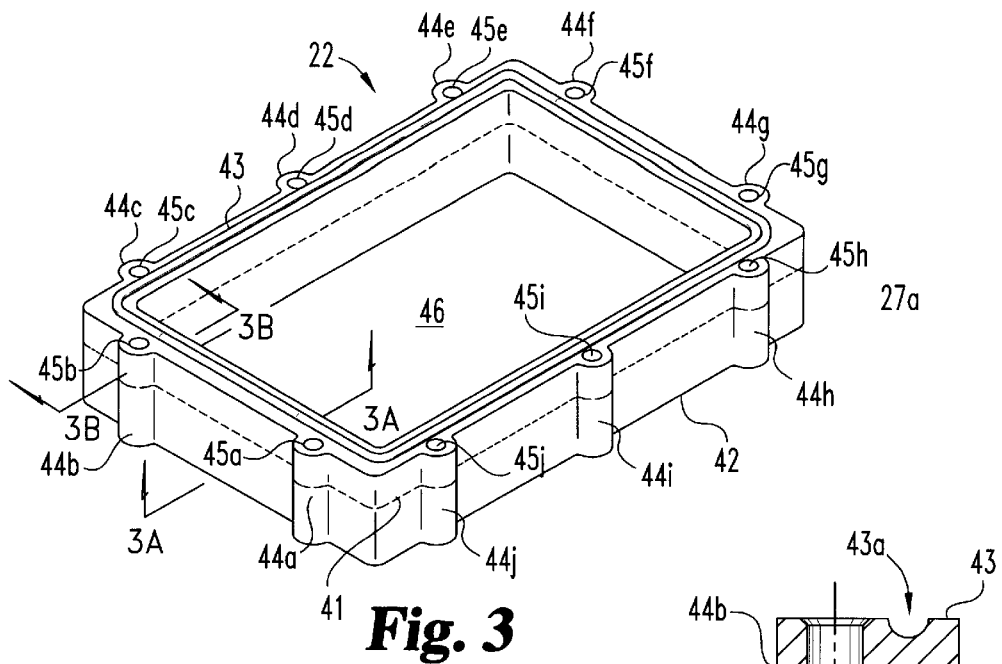
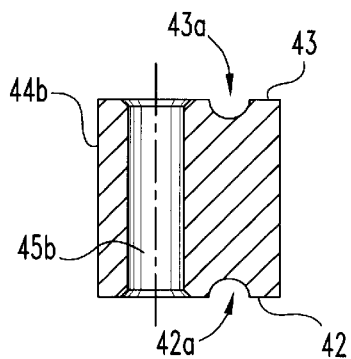
Fig. 3
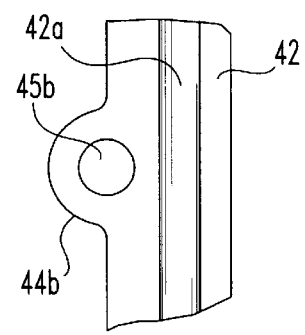
Fig. 3A
Fig. 3B
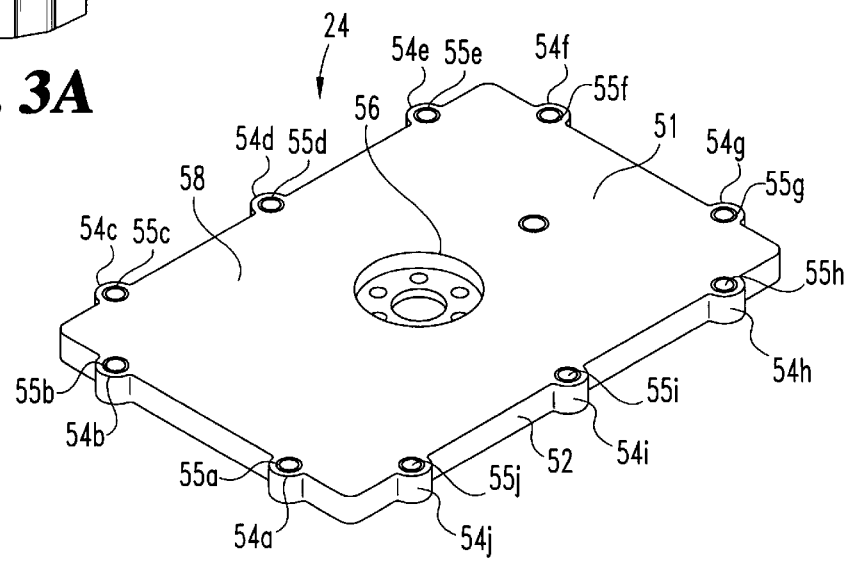
Fig. 4

STERILIZATION ASSEMBLY FOR INSTRUMENT CASE

BACKGROUND OF THE INVENTION

The present invention relates in general to instrument cases and trays which are designed to receive medical and/or dental implants and instrumentation for sterilization and thereafter use. Instrument cases and trays of the type disclosed herein are used to receive a wide variety of implants and instrumentation for special medical disciplines and procedures. More specifically the present invention relates to sterilization methods for instrument cases and the manner in which the design of the instrument case may or may not facilitate sterilization. The implants and instrumentation which are organized and stored in the cases and trays, or a combination thereof, remain organized and stored through the sterilization procedure and the storage period, awaiting call up for the next scheduled procedure.

The typical or conventional method of sterilization involves the placement of the instrument-loaded case, which has been double-wrapped in the prescribed manner, in an autoclave unit. The preferred wrapping is a woven paper material, known in the sterilization art. The sterilant, typically steam, is able to circulate over and around each of the instruments as well as throughout the case. The woven paper wrap is used to maintain a sterile condition while the instrument-loaded case is stored awaiting future use. This method presents a variety of concerns, including a limited shelf life, thirty to thirty-five days, a fairly expensive process in terms of time, material cost, and personnel, plus the necessity to dispose of the paper which was used to wrap the instrument case.

There is another method of sterilization which involves a more complex case design. However, this other method of sterilization provides a longer shelf life. Further, since there is no exterior paper wrapping, there is no wrapping paper to dispose of when the case is readied for use. This other method requires a deep drawn sterilizing holder case with one or more perforated panels in the lid and filter paper retained over these panels. The actual instrument case fits down inside of the sterilizing holder case. Prior to use, the instrument case is "flash" sterilized. As would be understood, this alternative method involves a more complex and expensive container, however, the shelf life, while extended (4 to 5 months) is still somewhat limited. This added expense will be amortized by saving on the wrapping paper, the wrapping labor, and the disposal costs.

In an effort to create a sterilizing method which provides a longer shelf life for the instrument case and in order to simplify the design complexity, the present invention was conceived. In the present invention, a conventional instrument case is loaded into a fixture which includes a base, collar, and lid, all of which are bolted together. The base provides an area for a room temperature sterilant (water) which will be heated and converted into steam for the sterilizing of the instruments which are loaded into the case. The lid includes a self-sealing steam release valve which automatically seals the fixture in a sterile fashion once the inside temperature reaches a sterile level. At a minimum, the inside temperature will be between 325 and 350 degrees Fahrenheit and may be somewhat higher.

While a variety of instrument cases and cassettes are known to exist and while there are a variety of sterilization methods, the present invention is novel and unobvious. The present invention provides a substantially longer shelf life with a design which has more functional versatility and flexibility than earlier designs and which is easier to use. A unique aspect of the present invention is that the sterilant is introduced into the device and then the device is sealed closed. This is the reverse of conventional and prior procedures and structures where the device is mechanically closed but "open" in order to receive an outside sterilant. The sterilant is "forced" into the device by gravity flow or migration.

SUMMARY OF THE INVENTION

A sterilization assembly for sterilizing an instrument case according to one embodiment of the present invention comprises a base including a flange surface and a liquid reservoir for receiving and retaining a sterilant, a collar constructed and arranged with oppositely-disposed first and second flange surfaces and a hollow interior which is constructed and arranged to receive at least one instrument case therein, a first elastomeric gasket positioned between the base flange surface and the first flange of the collar, a lid including a pressure-relief valve which is in a normally-closed condition, the lid having a flange surface, a second elastomeric gasket positioned between the lid flange surface and the second flange surface of the collar, threaded fasteners for securely joining together the lid and the base and thereby clamping the collar and the first and second elastomeric gaskets therebetween, this securely joined combination defining a fluid-tight (and pressure-tight) hollow interior and the pressure-relief valve being openable only due to a sufficiently high pressure in the hollow interior, the sufficiently high pressure being achievable by heating a sterilant in the liquid reservoir in order to create a sterilant vapor.

One object of the present invention is to provide an improved sterilization assembly for an instrument case.

Related objects and advantages of the present invention will be apparent from the following description.

BRIEF DESCRIPTION OF THE DRAWINGS

FIG. 3 is a perspective view of the collar which comprises another component of the FIG. 1 assembly.

FIG. 3A is a partial, bottom plan view of the FIG. 3 collar.

FIG. 3B is a partial, front elevational view in full section of the FIG. 3 collar.

FIG. 4 is a perspective view of the lid which comprises another component of the FIG. 1 assembly.

DESCRIPTION OF THE PREFERRED EMBODIMENT

Figure 1:
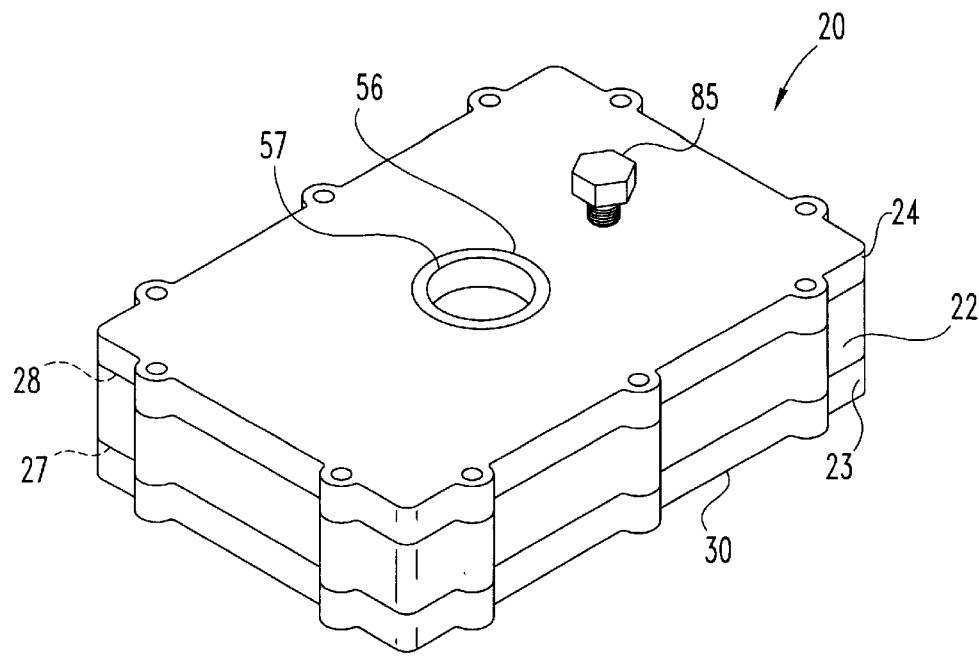
FIG. 1 is a perspective view of a sterilization assembly for an instrument case according to a typical embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 7:
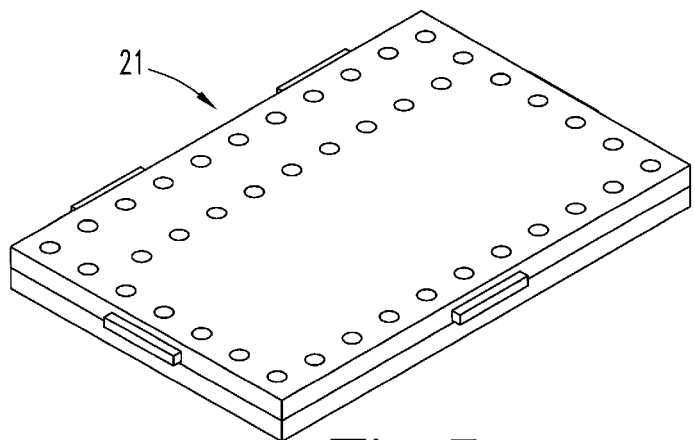
FIG. 7 is a perspective view of an instrument case which may be loaded into the FIG. 1 assembly according to the present invention.

Referring to FIG. 1 there is illustrated a sterilization assembly 20 which is designed to receive an instrument case (or tray) 21 (see FIG. 7) which case contains whatever medical or dental implants and instrumentation may be required for a particular procedure or procedures. As will be explained, instrument case 21 is able to be stacked onto a like instrument case and the only required change to the design of assembly 20 is to either increase the height of collar 22 and/or add additional collars so as to exceed the height of the stacked combination or grouping of instrument cases which are to be loaded into assembly 20.

Figure 1A:
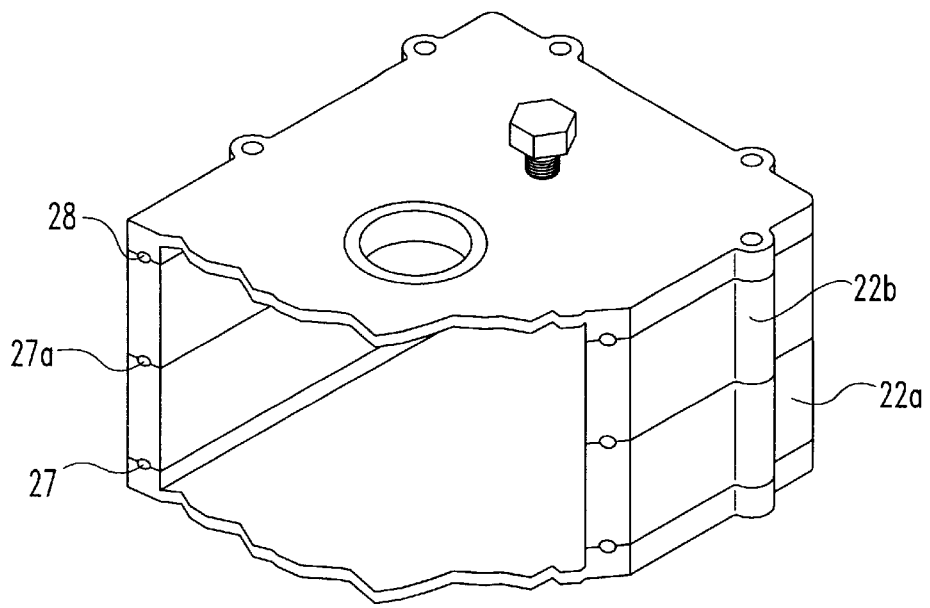
FIG. 1A is a partial, perspective view of the FIG. 1 assembly showing the use of two collars of equal depth according to the present invention.
Figure 1B:
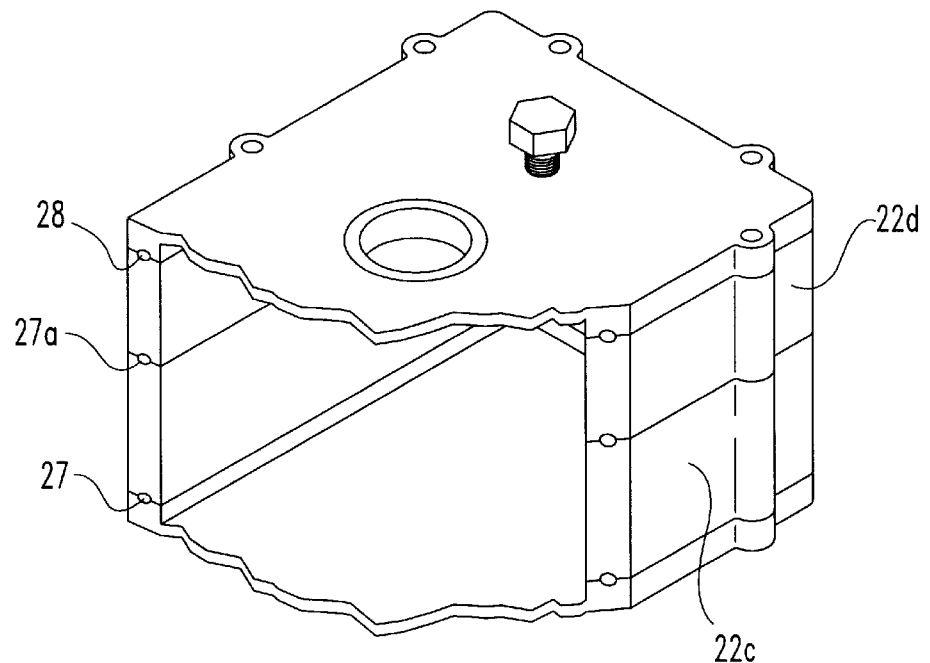
FIG. 1B is a partial, perspective view of the FIG. 1 assembly showing the use of two collars of different depth according to the present invention.

For examples of stacking variations for collar 22, refer to FIGS. 1A and 1B. In FIG. 1A, two collars 22a and 22b are stacked together to increase the interior clearance height within sterilization assembly 20. In this example, collars 22a and 22b are of equal height (i.e., depth) and are equal to the height of collar 22. In FIG. 1B, the two collars 22c and 22d which are stacked together are of different heights. Collar 22c is equal in height to collar 22 while collar 22d has a height which approximates one-half of the height of collar 22. Standard collar heights are preferably one inch, two inches, three inches, and four inches. However, virtually any height is acceptable, consistent with the teachings of the present invention. As the height of collar 22 (or the stack of multiple collars) increases, the length of the assembly screws will need to increase.

The base 23 and lid 24 designs of assembly 20 do not change regardless of the number of instrument cases 21 which are stacked together and loaded into assembly 20 and regardless of the height of collar 22 or the number of collars stacked together. As a practical matter, a stack of three or four instrument cases 21, assuming they are loaded with instruments, is probably the limiting number due principally to the time necessary to bring all of the case and instrument mass to the desired (required) sterilizing temperature. A less critical aspect of the "limiting number" is the overall weight of the assembly and the need to be able to safely lift and transport the assembly with the loaded instrument cases therein.

The theory of the present invention, which will be expanded upon, begins with an understanding that the base, collar, and lid are designed with flange areas in order to clamp down on and compress a corresponding peripheral gasket in order to create an enclosed and sealed hollow interior. Threaded fasteners, typically hexhead shoulder bolts, are used to draw the lid 24 and base 23 together and sandwich therebetween the collar 22 and two peripheral gaskets 27 and 28. Each peripheral gasket 27 and 28 has a solid circular cross section and is fabricated out of a medical-grade silicone with a durometer of between 60 and 70. Abutment between lid 24 and collar 22 prevents the over compression of gasket 28 while abutment between base 23 and collar 22 prevents the over compression of gasket 27. In order to maintain the resiliency of the elastomeric silicone material used for gaskets 27 and 28, it is important that the circular cross section not be compressed to the point that it becomes hard and looses its resiliency. When additional collars are used, such as in FIGS. 1A and 1B, additional peripheral gaskets 27a are required.

Figure 8:
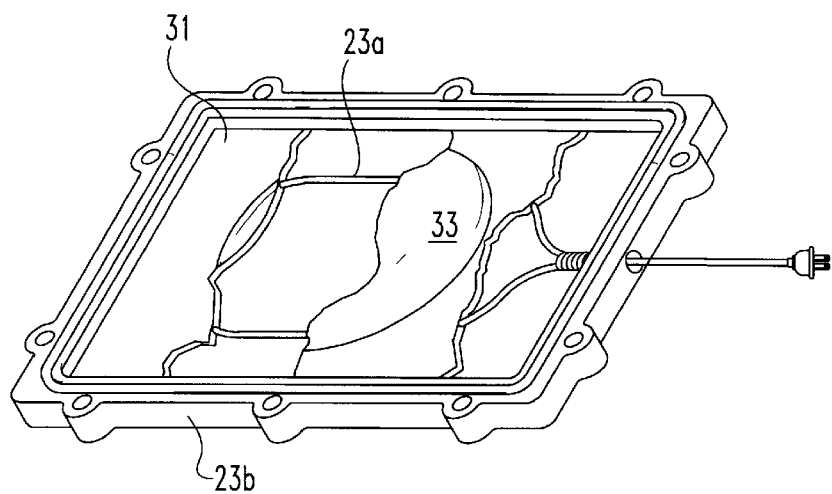
FIG. 8 is a perspective view of an alternative base for the FIG. 1 assembly incorporating a heating element.
Figure 9:
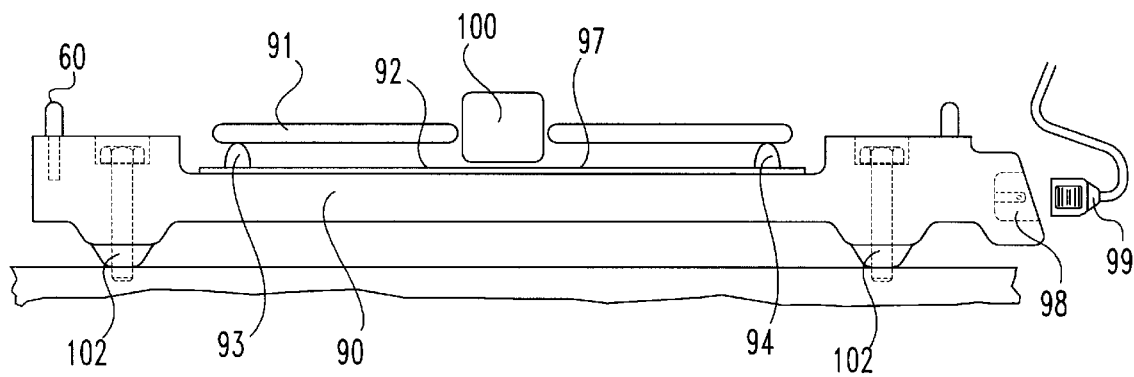
FIG. 9 is a diagrammatic, side elevational view of an alternative base design for the FIG. 1 assembly incorporating a heating element.

A sterilant reservoir 33 of a bowl-like shape is recessed in the upper surface 31 of the base and is used to hold a liquid sterilant which is captured inside of assembly 20. When the overall assembly 20 is placed in a conventional autoclave or on a heating element or heated surface, the liquid sterilant is converted to a vapor, i.e., steam, as the temperature of the assembly 20 increases. Once the interior temperature reaches a desired level, a pressure-relief valve in the lid opens and then automatically closes (spring-biased) once the inside pressure drops to a level below that at which the relief valve opens. The assembly is removed from the heat, and, as the temperature drops, the sterilant condenses and an interior vacuum is created which draws the lid and base together even that much tighter. As an alternative to the use of an autoclave or a heated surface or an external heating element, an internal heating element may be used. FIG. 8 illustrates one alternative to the base 23 of FIG. 2 by including a heating element (electrically operated) positioned within the underside of the base beneath surface 31 and sterilant reservoir 33. FIG. 9 illustrates another alternative to the base 23 of FIG. 2 and the base 23b of FIG. 8. Whatever type of heating is used, the upper temperature range has to be high enough for the present invention to perform as described herein.

Figure 2:
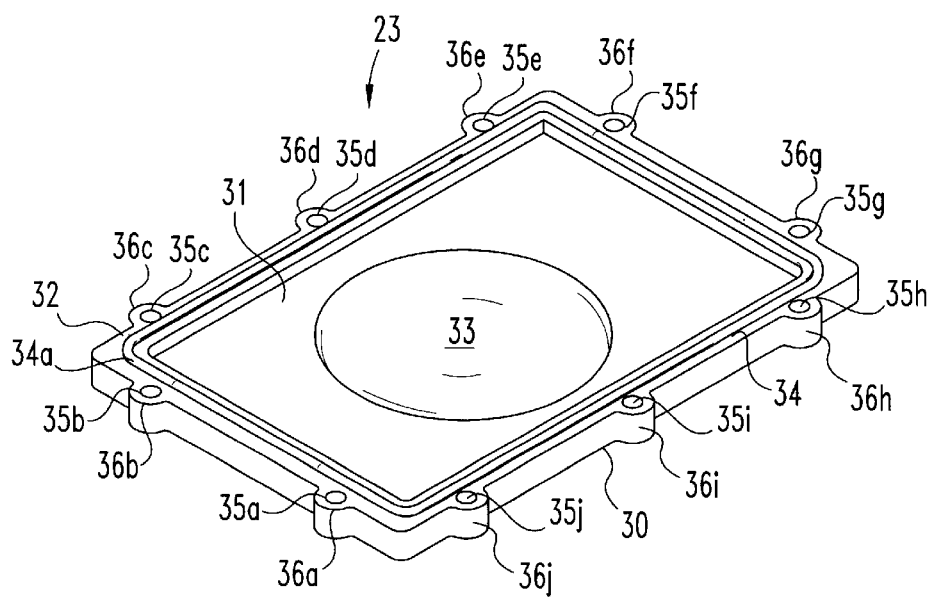
FIG. 2 is a perspective view of the base of the FIG. 1 assembly.

Considering now the individual component parts of sterilization assembly 20, the base 23 is illustrated in FIG. 2, the collar 22 is illustrated in FIG. 3, and the lid is illustrated in FIG. 4. Base 23 includes a substantially flat lower surface 30, a recessed inner surface (shelf) 31, a surrounding peripheral wall 32, a sterilant reservoir 33, and flange surface 34. Flange surface 34 is substantially flat and substantially parallel with lower surface 30. Machined into flange surface 34 is a peripheral gasket channel 34a which extends completely around the periphery of base 23 and which receives gasket 27. The cross section (lateral) geometry of channel 34a is illustrated in FIG. 2A with an alternative style 34b illustrated in FIG. 2B.

Figure 2A:
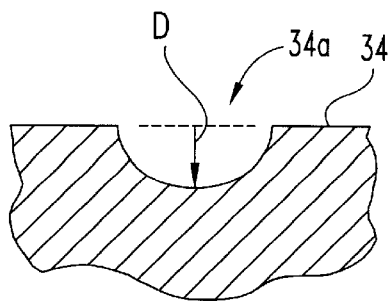
FIG. 2A is a partial, front elevational view in full section of a gasket channel comprising part of the FIG. 2 base.
Figure 2B:
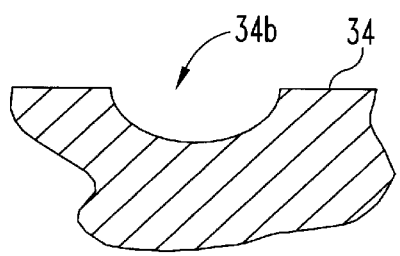
FIG. 2B is a partial, front elevational view in full section of an alternate shape for the FIG. 2A gasket channel.
Figure 2C:
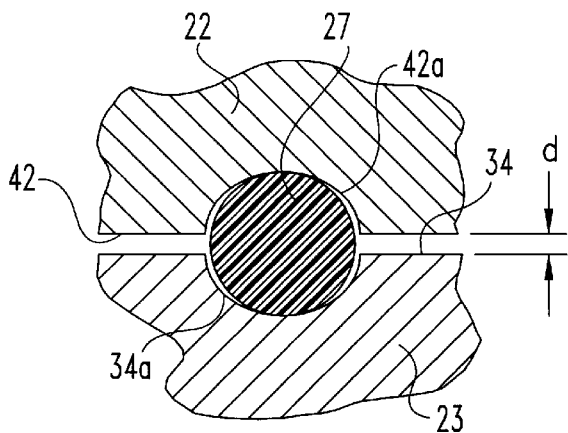
FIG. 2C is a diagrammatic, front elevational view in full section illustrating the manner in which a sealing gasket is captured between the base and collar of the FIG. 1 assembly.

In the FIG. 2A illustration, the lateral cross section through channel 34a shows that the curvature of the channel is circular with a depth (D) which is smaller than the radius of the gasket 27. A matching channel is machined into the facing peripheral surface of collar 22 with a comparable shape and depth to that of channel 34a. As such, the gasket 27 in a free state before the collar and base are drawn together created a separation between the facing surfaces of base 23 and collar 22. This arrangement is illustrated in FIG. 2C in which the gasket 27 and collar 22 have been added. As the collar and base are drawn together, gasket 27 is compressed and spreads out slightly to the sides (i.e., laterally) where clearance spaces exist. If it were to occur that the collar and base become clamped together such that the flange surfaces come in contact, the gasket 27 is still resilient so as to provide the desired and necessary sealing capability. The designed—in separation is shown as dimension (d).

The surrounding peripheral wall 32, in cooperation with flange surface 34, defines bolt holes 35a–35j. Each bolt hole 35a–35j needs to be configured for the threaded engagement with a corresponding fastener. Each bolt hole is fitted with a threaded insert or threaded sleeve in the preferred embodiment. Alternatively each bolt hole 35a–35j can be internally threaded. Bosses 36a–36j which surround each bolt hole provide added strength to the overall assembly as well as a larger bearing surface against face gasket 27. The bolt hole locations and the corresponding boss locations are spaced apart so to balance and distribute the clamping forces of the bolts which are inserted through the lid 24 and collars into the base 23. Accordingly, holes 35a and 35b are aligned with holes 35g and 35f, respectively. Holes 35c, d, and e are aligned with holes 35j, i, h, respectively. Channel 34a extends around the periphery of the base 23 inside of the bolt holes 35a–35j so as to not interfere with the bolt holes.

The thickness of the base 23 between lower surface 30 and inner surface 31 is sufficient to receive the recessed sterilant reservoir 33 which is approximately ¾ inch deep. In the case of FIG. 8 the base is deep enough to also include heating element 23a. Reservoir 33 is filled with a liquid sterilant, which could be distilled water, and which is converted to a vapor (steam) when the lower surface 30 is placed on a burner or heating element. As an alternative and as mentioned with regard to FIG. 8, a heating element 23a can be implanted within the lower portion of the base, now base 23b, so as to directly heat the base in order to create the sterilant vapor. An alternative heating arrangement is illustrated in FIG. 9 and is described in greater detail hereinafter. By means of an electrically operated heating element 23a, the present invention can be used at remote sites from either a portable generator or car battery. With regard to base 23, the shape of reservoir 33 as well as the number of smaller, similar reservoirs, if that is elected as an option, is not critical as the purpose is simply to be able to provide a reservoir of sufficient capacity for the selected sterilant.

Figure 2D:
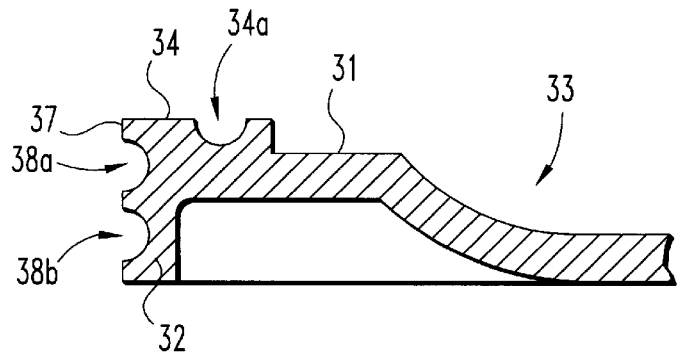
FIG. 2D is a partial, front elevational view in full section illustrating a weight reduction approach for the base of the FIG. 1 assembly.

In order to reduce the weight of base 23 without compromising the strength of base 23 and the suitability of base 23 for its intended function, metal can be removed in a careful and selective fashion. The outer surface 37 of each side wall 32 can be modified in between the bosses 36a–36j with grooves 38a, 38b, to reduce the weight as is illustrated in FIG. 2D. The underside of base 23 can also be contoured as shown in FIG. 2D to reduce the weight of base 23. The shelf 31 which extends completely around the reservoir 33 provides a substantially flat surface for the support of one or more instrument cases or trays.

With reference to FIG. 3, the collar 22 is configured as a frame 41 with a substantially flat lower flange surface 42 which is of the same size and shape as flange surface 34. Frame 41 also includes a substantially flat upper flange surface 43 which is of the same size and shape as flange surface 42 and is substantially parallel to flange surface 42. The frame is constructed so as to surround an interior space 46 and includes ten bosses 44a–44j which define ten clearance holes 45a–45j. The size, shape, location, and spacing of bosses 44a–44j are substantially the same as bosses 36a–36j. Likewise, the size, shape, location, and spacing of holes 45a–45j is substantially the same as holes 35a–35j.

Machined into lower flange surface 42 is a peripheral gasket channel 42a which has a size, shape and location which are substantially the same as channel 34a (relative to flange surface 34). The location of channel 42a is illustrated in FIG. 2C as well as in FIGS. 3A and 3B. As previously explained, channels 34a and 42a cooperate to capture gasket 27. Since this portion of the description is directed to the lower flange surface 42, FIG. 3A is a bottom plan view. FIG. 3B is turned 180 degrees so as to agree with the orientation of collar 22 in FIG. 2C. As will be described, the upper flange surface 43 includes a gasket channel 43a which is axially aligned with channel 42a.

The relationship between flange surfaces 42 and 34 and between channels 42a and 34a for the capture of gasket 27 is repeated and in effect duplicated for flange surface 43 of the collar and flange surface 53 (see FIG. 4) of the lid 24. Likewise, flange surface 53 includes a gasket channel 53a which is designed to cooperate with channel 43a for the capture of gasket 28.

The interior space 46 defined by frame 41 is sized and shaped, including its height, so as to accommodate the size and number of instrument cases which are to be loaded into assembly 20 for sterilizing. As previously described, it is envisioned that the collar heights will be standardized in 1 inch, 2 inch, 3 inch, and 4 inch heights and combined as desired to achieve whatever collar height (or depth) is needed. While these standard heights represent the most likely, it will also be understood that greater collar heights are possible, though in going to larger or greater heights, some of the versatility will be compromised. Since each collar includes its own gasket channels in the top and bottom flange surfaces, sealed interfaces are created on each side collar 22 regardless of the stack up of multiple collars. A broken line is used to represent that a plurality of different (or the same) height collars can be stacked together. The stack of collars is also illustrated in FIGS. 1A and 1B. It is to be understood that the collar is the only component which would need to be changed (except for the bolt length) as the number of instruments cases is increased or decreased.

With reference to FIG. 4, lid 24 includes an upper wall 51, a surrounding peripheral wall 52, a lower flange 53 at the base of wall 52, bosses 54a–54j, bolt holes 55a–55j, valve aperture 56, and top surface 58. Assembled into valve aperture 56 is a pressure-relief valve 57 (see FIG. 6). Each bolt hole 55a–55j is configured with a shallow counterbore for receipt of a stainless steel washer. Cooperating stainless steel hexhead bolts and stainless steel washers are used to securely connect the base 23, collar 22, and lid 24 together. Alternatively, each bolt hole 55a–55j can be counterbored with adequate clearance for the head of a sockethead shoulder bolt. The size, shape, location, and spacing of bosses 54a–54j are substantially the same as bosses 44a–44j and bosses 36a–36j. Likewise, the size, shape, location, and spacing of holes 55a–55j are substantially the same as holes 45a–45j and holes 35a–35j.

Figure 4A:
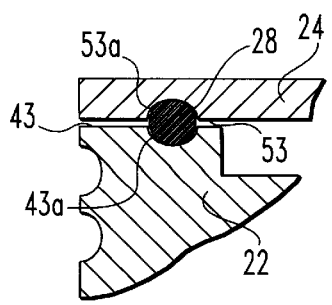
FIG. 4A is a partial, front elevational view in full section illustrating the capture of a sealing gasket between the lid and collar of the FIG. 1 assembly.
Figure 5:
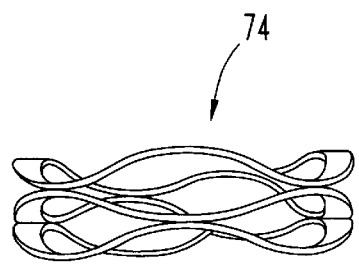
FIG. 5 is a front elevational view of a compression spring comprising a portion of the FIG. 1 assembly.

Lower flange surface 53 includes a peripheral gasket channel 53a which is sized, shaped, and located similar to channel 43a for capturing gasket 28 and for the compression of gasket 28 in order to create a sealed interface between the lid 24 and the collar 22, see FIG. 4A. Regardless of the number or size of collars 22 which may be stacked together, the clamping onto gasket 28 between the lid 24 and the (top) collar remains unaffected. The only change is in the length of the bolts used to clamp the base, collar(s) and lid together and to compress gaskets 27 and 28 and any gaskets used between any additional collars which may be stacked together.

The lower flange 53 is substantially flat and has a size and shape which is substantially the same as upper flange surface 43 of collar 22. The substantially flat nature of the flanges and flange surfaces is important for clamping the peripheral gaskets 27 and 28 so as to create an enclosed and sealed interior for assembly 20.

In the preferred embodiment, ten hexhead bolts are inserted through the ten bolt holes, starting with those bolt holes in the lid 24 and continuing passed the first gasket, through the collar, passed the second gasket and into the base. Each receiving bolt hole 35a–35j is threadedly configured to receive the inserted end of the corresponding bolt. This threaded configuration is preferably an insert or threaded sleeve, but could alternatively be internally-threaded or receive a hex nut. As the bolts and the cooperating inserts are tightened, the peripheral gaskets 27 and 28 are compressed and the collar 22 is securely clamped between the base and lid.

As assembly 20 is bolted together, the lid draws towards the top surface of collar 22 and the base draws towards the underside or lower surface of collar 22. As this occurs, gaskets 27 and 28 are compressed and their original thickness decreases. If this continues, the gaskets could be over compressed and become too rigid to remain resilient, though the resilient gaskets must still be firm enough to withstand atmospheric pressure. However, once (if) the facing and adjacent flange surfaces are drawn into abutment, the gasket compression stops. At this point, the gaskets are fully compressed for a tight seal but not beyond the point where they are not resilient. This is ensured by properly setting the initial separation between facing and adjacent flange surfaces relative to the gasket diameter and durometer. The key is to still have gasket resiliency left if or when the flange surfaces abut. In this tightly clamped and sandwiched assembly, the gaskets provide a leak tight combination against any possible escape of sterilant vapor. As the sterilant vapor condenses, a vacuum is created in the sealed interior of assembly 20. Since this vacuum draws the lid and collar closer together and the base and collar closer together, clearances are designed between these components. This designed-in clearance permits some degree of further movement for tighter compression of gaskets 27 and 28 in response to the vacuum and outside atmospheric pressure.

Figure 10:
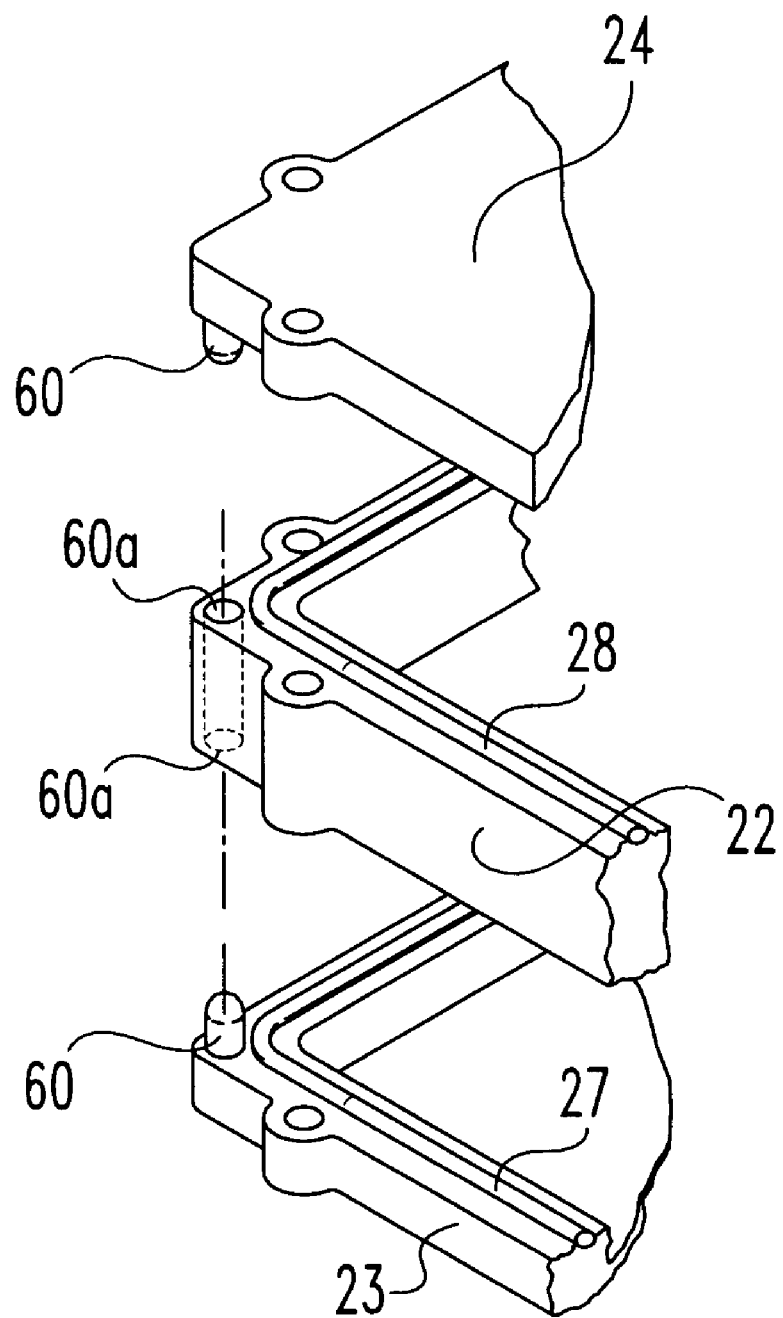
FIG. 10 is a partial, exploded perspective view of an alignment pin and bore combination for the FIG. 1 assembly.

As an added alignment feature option (see FIG. 10), the base 23, collar 22, and lid 24, are configured to accommodate alignment pins 60. Each alignment pin 60 is designed to fit closely within a matching bore 60a which is precisely machined into the adjacent metal component. In the preferred embodiment, two pins 60 are anchored into diagonally-opposite corners of the upper surface of base 23 with matching bores machined into the lower surface of collar 22. By fitting the two pins into the two matching bores, the base and collar are precisely positioned one relative to the other. This guarantees that the connecting hardware will properly align itself through the various clearance holes and bores in these primary frame components. Further, as is illustrated in FIG. 10, two pins 60 are anchored into diagonally-opposite corners of the lower surface of lid 24 with matching bores machined into the upper surface of collar 22. The partial, exploded perspective view of FIG. 10 actually discloses only one of the two corners, and thus it should be understood that the opposite diagonal corner is configured in a virtually identical fashion to that which is illustrated.

By designing the pins 60 and matching machined bores 60a with a close fit, and by placing these pins at diagonally-opposite corners, the correct alignment and assembly of the three primary flame components is assured.

Figure 6A:
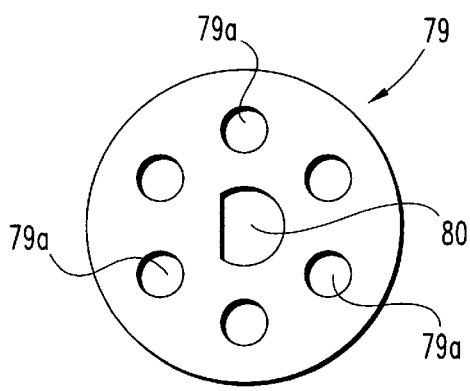
FIG. 6A is a top plan view of a washer comprising a portion of the FIG. 6 valve.
Figure 6B:
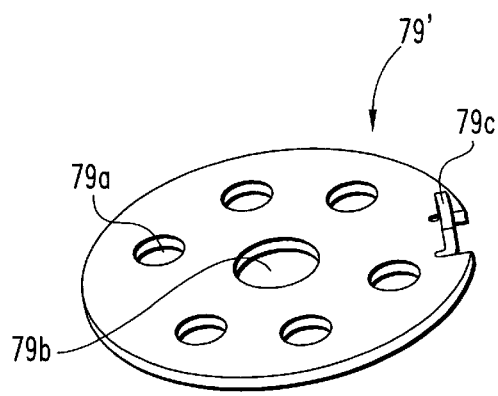
FIG. 6B is a perspective view of an alternate washer configuration suitable for use as part of the FIG. 6 valve.
Figure 6:
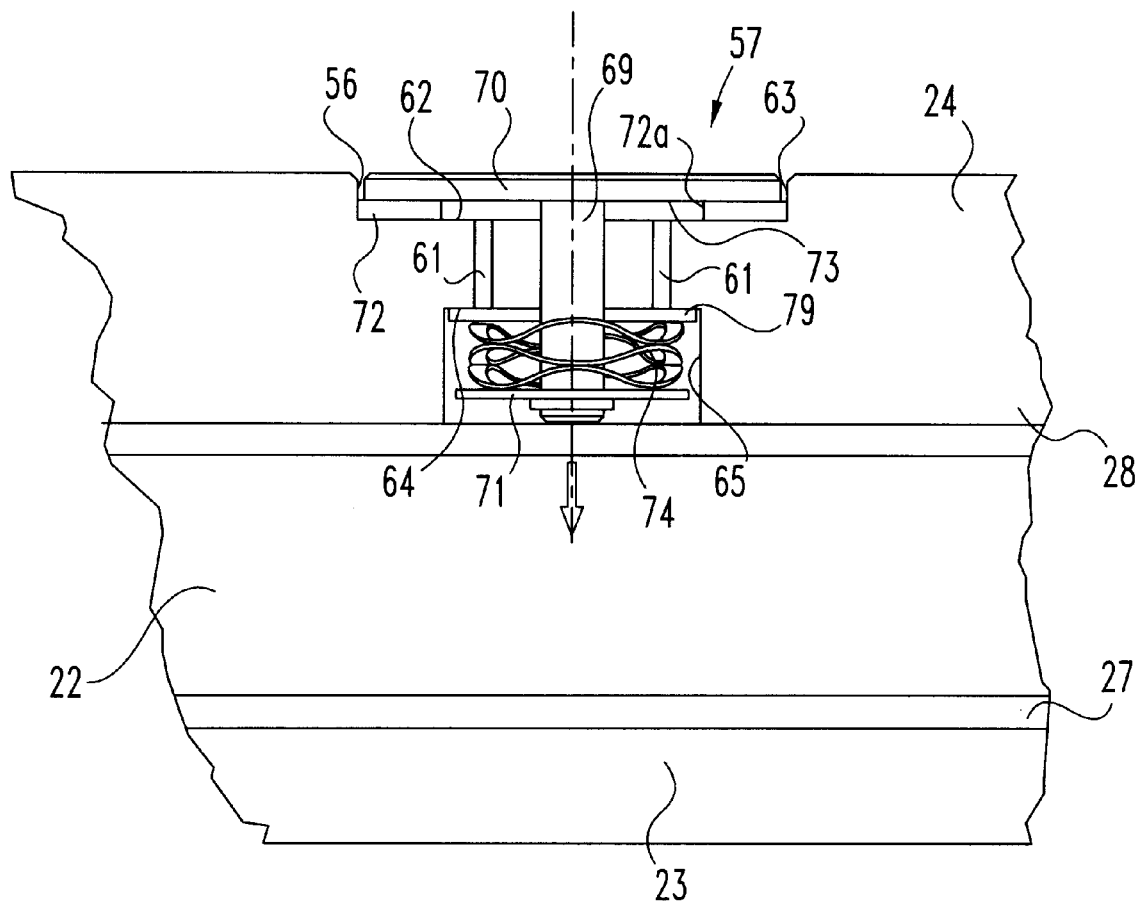
FIG. 6 is a partial, side elevational view in full section of the pressure-relief valve of the FIG. 1 assembly.

Referring to FIG. 6, the pressure-relief valve 57 and its manner of assembly into the valve aperture 56 of lid 24 is illustrated in greater detail and in cross section. Valve aperture 56 is counterbored from both sides and six, equally-spaced vent apertures 61 are drilled through lid 24 in a concentric pattern inside of valve aperture 56. One end of each vent aperture 61 intersects the base or bottom surface 62 of counterbore 63 and the other end of each vent aperture 61 intersects the base 64 of counterbore 65.

Pressure-relief valve 57 includes a moveable plunger comprising a valve stem 69 with an enlarged cylindrical disk 70 at one end and a retaining ring 71 at the opposite end. Also included is an annular, elastomeric sealing gasket 72 positioned at the base 62 of counterbore 63. The size of the interior opening 72a of gasket 72 enables the six vent apertures to open into the counterbore interior space and direct any flow through the vent aperture directly against the inside or underside surface 73 of disk 70. Captured on stem 69 and seated against retaining ring 71 is a flat wire compression spring 74 which has a wave-like shape of multiple layers. Spring 74 (see FIG. 6A) includes a plurality of layers 75 with an alternating pattern of raised waves and recessed depressions. A suitable product for spring 74 is a SPIRAWAVE® spring offered by Smalley Steelring Company of Wheeling, Ill.

In the FIG. 6 illustration, a hardened steel washer 79 is positioned between the spring 74 and the base 64 of the counterbore 65 on the underside of lid 24. Since the lid is preferably made of aluminum, and since the spring 74 is made of stainless steel, continued use of sterilization assembly 20 could result in wear against the aluminum material of the lid and with continued use could create ruts in the aluminum which would interfere with the correct operation of the spring 74. The hardened stainless steel washer 79 includes six clearance holes 79a which are in alignment with the six vent apertures 61.

In order to maintain the hardened steel washer in the proper alignment so that the clearance holes 79a remain in alignment with the vent apertures 61, the interior of the steel washer 79 (see FIG. 6A) is provided with a D-shaped aperture 80 and at its corresponding position on stem 69, a D-flattened surface is provided. Alternatively, a circular clearance hole 79b can be used to replace the D-shaped aperture 80 and a bent tab 79c (see FIG. 6B) is used to fix the position of the washer 79' for alignment of the six clearance holes 79a with the six vent apertures 61. The bent tab is inserted into a drilled hole in the lid 24 outwardly of the vent apertures. The spring 74 holds the bent tab in position and the insertion into the drilled hole in the lid keeps the washer 79' from turning.

In the FIG. 6 illustration, the pressure-relief valve is in a closed condition and in this condition the spring 74 has been compressed and flattened to a degree that it tries to return to a more expanded height. As the spring tries to return, a spring biasing force is created. As a result, the layers 75 of spring 74 are pushed downwardly against the base 64 of counterbore 65. In turn, since the base cannot move, this causes a pushing force against the retaining ring 71. A downward force on retaining ring 71 pulls downwardly on stem 69 and disk 70 such that the inside surface 73 of disk 70 is drawn tightly against gasket 72, tightly sandwiching the gasket between the base 62 and the inside surface 73 of disk 70. This creates a fluid-tight interface completely sealing closed the interior of assembly 20. The tightness of the sealed interface is governed by the spring constant of spring 74 and the distance between the retaining ring and the inside surface 73 of disk 70. In order to push the disk 70 off of gasket 72, and thereby vent the interior of assembly 20, an interior pressure must be created which is able to overcome the spring biasing force created by spring 74.

With reference to FIG. 9 an alternative base design is illustrated. Base 90 includes a CAL-ROD heating element 91 which is centered within the upper surface 92 of base 90 and which rests on supports 93 and 94. Base 90 includes a stainless steel, heat reflective support sheet 97 which is positioned on upper surface 92. One end of base 90 is designed and hard wired with a 220 volt socket 98. The heating element 91 is wired to this socket 98 and a power cord 99 is used to provide electricity to the heating element. A temperature control module 100 is included as part of the heating element and permits the user to set the desired temperature which is to be maintained. A thermostat control as part of this temperature control module helps to maintain the correct and desired temperature.

In order to serve as more of a thermal insulator and thus make handling easier, a suitable material for base 90 is a fiberglass-filled, ceramic, heat-resistant material. Additionally, insulator support feet 102 are provided to keep whatever surface the base 90 rests upon at a lower temperature. In this way there is greater versatility for the use of sterilization assembly 20 and for the support surface which is used.

In operation, the sterilization assembly 20 is first assembled, placing the instrument cases 21 to be sterilized in position and selecting a suitable collar or collars 22 based upon the overall height requirement. The sterilant reservoir 33 is then filled with whatever sterilant is going to be used, such as distilled water for steam. Hexhead bolts, each of a suitable length, are inserted into the lid, through the collar, and received by corresponding internally threaded inserts or threaded sleeves which are inserted in the bolt holes 35a–35j in a flush to recessed manner relative to lower surface 30. As the bolts are tightened, the three metal components, the lid 24, collar 22, and base 23 are drawn tightly together, clamping therebetween the peripheral gaskets 27 and 28. With the pressure-relief valve 57 assembled and in a spring-biased and closed condition, the interior of the sterilization assembly 20 is completely sealed in a fluid- tight manner. The next step is to place the assembly 20 in an autoclave or on a burner or heating element and convert the water (sterilant) to steam. As an alternative, if the base is configured with an inserted heating element (see FIGS. 8 and 9), the element simply needs to be plugged in or connected to a source of electricity for the heating of the sterilant. The heating process will take some time because the entire assembly, including all of the instruments which are loaded into the cases, act as heat sinks, and these must be brought to an elevated temperature. As the interior temperature increases, steam is produced and the interior pressure gradually increases. When the interior temperature reaches an acceptable sterilization temperature, presently in excess of 275 degrees F., the steam pressure inside the sterilization assembly 20 is high enough to overcome the spring force of spring 74 and thereby lift the disk 70 away from gasket 72. At the instant these two members separate, some of the steam is released and immediately the interior pressure reduces to a level which is no longer able to exceed the spring force of the spring 74. Consequently, just as quickly as the disk opened in order to vent the steam, the disk closes back against gasket 72.

By proper design and by setting the right relationships, the pressure-relief valve does not release until the interior temperature of the overall assembly, including the instrument cases and all the instruments which are loaded therein, are at a suitable sterilization temperature, such as 350 degrees Fahrenheit. The escape of steam represents an exit flow which (1) prevents any simultaneous inflow of outside air and (2) reduces the steam volume inside of sealed sterilization assembly 20. When the sterilization assembly 20 is then removed from the heat or the heating element is disconnected, the interior gradually cools and as the sterilant condenses, a vacuum is created and this creates a suction force which tightly pulls the lid and base together, clamping between these two components the collar and the two gaskets. This tightly clamped combination creates a fluid-tight assembly around the instrument cases which are loaded therein. The sterilized instruments are thus able to be maintained in this condition for at least one (1) year and in all likelihood much longer without any risk that the sealed assembly will be violated. A threaded pressure plug 85 (see FIG. 1) is tightly anchored into lid 24 and is used to release the vacuum when the instruments loaded within the instrument cases are required for use. By unscrewing, at least in part, pressure plug 85, atmospheric air at a higher pressure than that in the interior of assembly 20 is able to enter and this releases the suction force, enabling the ten hexhead bolts to be more easily loosened in order to separate the lid from the collar and allow the instrument cases which were loaded therein to be removed.

One advantage of the present invention is that the instrument cases are stacked before the collars are positioned around them and, accordingly, those cases are made readily accessible when the collars are lifted off of the base prior to use. In the interest of space economy in the autoclave, the instrument case which is to be placed in the sterilization assembly 20 and the internal measurements of assembly 20 are limited and prescribed by DIN size or European specifications. Consequently, the instrument cases, out of necessity, are sized as large as possible to hold the implants and instrumentation and yet still fit closely in the sterilization assembly 20. As a result, it is not easy to retrieve one or more instrument cases up and out of the sterilization assembly, unless the collar is removable. This highlights one of the deficiencies and drawbacks of other similar systems which do not have the removable collar. In these earlier systems, the side wall of the sterilization case or assembly remains fixed with the base and it is difficult for a user to gain access to the instrument case due to the close fit between the outside dimensions of the case and the inside dimensions of the sterilization assembly. The present invention solves this problem by allowing the lid and the collar to be removable such that the instrument case or cases which are loaded into the sterilization assembly are accessible from all sides and easily grasped by the user once the collar or collars are removed.

Another distinct advantage of this design is the fact that, contrary to currently used sterilization cases which are deep drawn tubs of fixed depth, the present invention permits a variable depth, depending on the number of instrument cases which are to be stacked and sterilized within sterilization assembly 20. This feature has been discussed and illustrated, noting the concept of having standardized collar heights in one inch, two inch, three inch, and four inch dimensions which can then be mixed and matched to create virtually any overall collar height. The only change, as a series of different collars are stacked together to achieve the desired height, is that the clamping bolts which extend through the lid and into the base must have a corresponding increase in their length.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A sterilization assembly for sterilizing an instrument case comprises:

a base including a flange surface and means for receiving a sterilant;

a collar constructed and arranged with oppositely disposed first and second flange surfaces, said collar having a frame construction which surrounds an interior space which is sized and shaped to receive at least one instrument case therein;

a first elastomeric gasket positioned between the base flange surface and the first flange surface of said collar;

a lid including a pressure-relief valve which is in a normally-closed condition, the lid having a flange surface;

a second elastomeric gasket positioned between said lid flange surface and the second flange surface of said collar;

means for securely joining together the lid and the base and thereby clamping the collar and the first and second elastomeric gaskets therebetween, the securely joined combination of the lid, base and collar defining a fluid-tight hollow interior; and said pressure-relief valve being openable due to a sufficiently high pressure in said hollow interior, said sufficiently high pressure being achievable by heating a sterilant in said base to create a sterilant vapor.

2. The sterilization assembly of claim 1 wherein said base flange surface defines a gasket channel for receipt of said first elastomeric gasket and the first flange surface defines a gasket channel for cooperating receipt of said first elastomeric gasket.

3. The sterilization assembly of claim 2 wherein said lid flange surface defines a gasket channel for receipt of said second elastomeric gasket and the second flange surface defines a gasket channel for cooperating receipt of said second elastomeric gasket.

4. The sterilization assembly of claim 3 wherein said means for receiving a sterilant includes a recessed reservoir.

5. The sterilization assembly of claim 4 wherein said means for securely joining together the lid and the base includes a plurality of threaded fasteners, a plurality of clearance holes in said lid and in said collar, and a plurality of cooperating threaded members received within said base.

6. The sterilization assembly of claim 5 wherein said pressure-relief valve includes a spring member and a moveable plunger.

7. The sterilization assembly of claim 6 wherein said lid defines a valve opening and said sterilization assembly further includes a sealing gasket positioned in said valve opening.

8. The sterilization assembly of claim 7 wherein said spring member is constructed and arranged to spring bias said moveable plunger into sealing contact against said sealing gasket.

9. The sterilization assembly of claim 1 wherein said means for receiving a sterilant includes a recessed reservoir.

10. The sterilization assembly of claim 1 wherein said means for securely joining together the lid and the base includes a plurality of threaded fasteners, a plurality of clearance holes in said lid and in said collar, and a plurality of cooperating threaded members received within said base.

11. The sterilization assembly of claim 1 wherein said pressure-relief valve includes a spring member and a moveable plunger.

12. The sterilization assembly of claim 11 wherein said lid defines a valve opening and said sterilization assembly further includes a sealing gasket positioned in said valve opening.

13. The sterilization assembly of claim 12 wherein said spring member is constructed and arranged to spring bias said moveable plunger into sealing contact against said sealing gasket.

14. The sterilization assembly of claim 1 wherein said base includes a heating element for elevating the temperature of any sterilant in said means for receiving a sterilant.

15. A sterilization assembly for sterilizing an instrument case comprises:

a base including means for receiving a sterilant;

a collar having a frame construction which surrounds an interior space which is sized and shaped to receive at least one instrument case therein;

a first elastomeric gasket positioned between said base and said collar;

a lid including a pressure-relief valve which is in a normally-closed condition;

a second elastomeric gasket positioned between said lid and said collar;

means for securely joining the lid and the base and thereby clamping the collar and the first and second elastomeric gaskets therebetween, the securely joined combination of the lid, base and collar defining a fluid-tight hollow interior; and said pressure-relief valve being openable due to a sufficiently high pressure in said hollow interior, said sufficiently high pressure being achievable by heating a sterilant in said base to create a sterilant vapor.

16. The sterilization assembly of claim 15 wherein said means for receiving a sterilant includes a recessed reservoir.

17. The sterilization assembly of claim 16 wherein said means for securely joining together the lid and the base includes a plurality of threaded fasteners, a plurality of clearance holes in said lid and in said collar, and a plurality of cooperating threaded members received within said base.

18. The sterilization assembly of claim 17 wherein said pressure-relief valve includes a spring member and a moveable plunger.

19. The sterilization assembly of claim 18 wherein said lid defines a valve opening and said sterilization assembly further includes a sealing gasket positioned in said valve opening.

20. The sterilization assembly of claim 19 wherein said spring member is constructed and arranged to spring bias said moveable plunger into sealing contact against said sealing gasket.

21. The sterilization assembly of claim 15 wherein said means for securely joining together the lid and the base includes a plurality of threaded fasteners, a plurality of clearance holes in said lid and in said collar, and a plurality of cooperating threaded members received within said base.

22. The sterilization assembly of claim 15 wherein said pressure-relief valve includes a spring member and a moveable plunger.

23. The sterilization assembly of claim 22 wherein said lid defines a valve opening and said sterilization assembly further includes a sealing gasket positioned in said valve opening.

24. The sterilization assembly of claim 23 wherein said spring member is constructed and arranged to spring bias said moveable plunger into sealing contact against said sealing gasket.

25. The sterilization assembly of claim 15 wherein said base includes a heating element for elevating the temperature of any sterilant in said means for receiving a sterilant.

* * * * *

UNITED STATES PATENT AND TRADEMARK OFFICE
CERTIFICATE OF CORRECTION

PATENT NO. : 6,010,670
DATED : January 4, 2000
INVENTOR(S) : Bernie B. Berry, Jr.

It is certified that error appears in the above-identified patent and that said Letters Patent is hereby corrected as shown below:

In Col. 7, at line 59, replace "comers" with -- corners --.

In Col. 7, at line 67, replace "comers" with -- corners --.

In Col. 8, at line 3, replace "comers" with -- corners --.

In Col. 8, at line 5, replace "comer" with -- corner --.

In Col. 8, at line 9, replace "comers" with -- corners --.

In Col. 8, at line 10, replace "flame" with -- frame --.

Signed and Sealed this

First Day of August, 2000

*Attest:*

Q. TODD DICKINSON

*Attesting Officer*         *Director of Patents and Trademarks*